United States Patent [19]

Feingold

[11] Patent Number: 4,784,646
[45] Date of Patent: Nov. 15, 1988

[54] SUBCUTANEOUS DELIVERY DEVICE

[76] Inventor: Vladimir Feingold, 6/15 Carrington Road, Castle Hill, New South Wales 2154, Australia

[21] Appl. No.: 937,232

[22] Filed: Dec. 3, 1986

[30] Foreign Application Priority Data

Dec. 3, 1985 [AU] Australia .............. PH3700

[51] Int. Cl.⁴ .............................................. A61M 5/32
[52] U.S. Cl. ......................................... 604/175; 604/9
[58] Field of Search ............... 604/175, 891, 116, 117, 604/8-10, 247; 128/1 R, DIG. 25

[56] References Cited

U.S. PATENT DOCUMENTS

| | | | |
|---|---|---|---|
| 4,338,937 | 7/1982 | Lerman | 604/891 |
| 4,360,019 | 11/1982 | Portner et al. | 604/891 |
| 4,465,062 | 8/1984 | Versaggi et al. | 604/247 |
| 4,496,349 | 1/1985 | Cosentino | 604/175 |
| 4,502,502 | 3/1985 | Krug | 604/247 |
| 4,581,018 | 4/1986 | Jassawalla et al. | 604/891 |
| 4,610,658 | 9/1986 | Buchwald et al. | 604/9 |
| 4,657,536 | 4/1987 | Dorman | 604/9 |
| 4,676,772 | 6/1987 | Hooven | 604/9 |

Primary Examiner—John D. Yasko
Attorney, Agent, or Firm—Ladas & Parry

[57] ABSTRACT

A subcutaneous delivery device assembly and method is provided. The assembly includes a subcutaneous delivery device comprising a catheter, a self-sealing input port at a first end of the catheter, an internal magnet adjacent to the self-sealing port and a valve at a second end of the catheter. The assembly further includes a corresponding external locator which is adapted to be magnetically located adjacent to the internal magnet and separator therefrom by a thin layer of human tissue. The assembly can be used to locate and stabilize a syringe needle during injection.

11 Claims, 1 Drawing Sheet

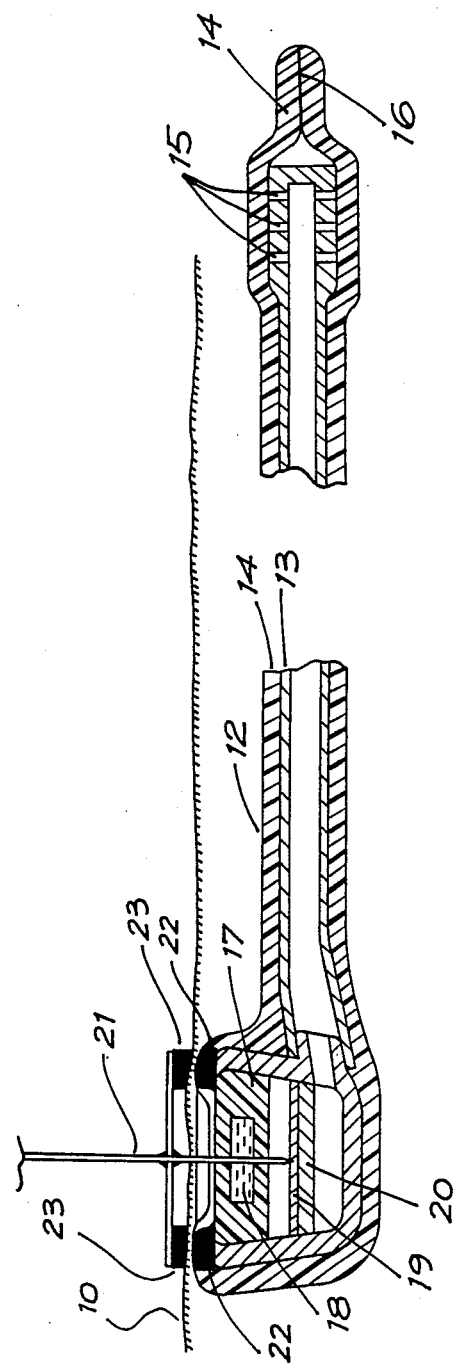

SUBCUTANEOUS DELIVERY DEVICE

BACKGROUND OF THE INVENTION

The present invention relates to a subcutaneous delivery device. In particular the invention is directed to a catheter with novel coupling means designed to remain implanted under the skin of the user.

Medication is introduced into a body either orally or by hypodermic syringe. Some medication is not able to be taken orally and must be injected by hypodermic syringe. Such injection however, is localised around the syringe needle and relies on distribution in the bloodstream to reach the organ to be treated. The effect of the medication is therefore diluted and delayed.

The present invention seeks to overcome this problem by providing a subcutaneous delivery device which provides direct delivery of medication to the organ vein, artery or region of the body to be treated. Moreover, the subcutaneous delivery device of the present invention uses magnetic coupling to the delivery syringe to locate and stabilize the syringe needle during injection.

SUMMARY OF THE INVENTION

In one broad form, the invention provides a subcutaneous delivery device comprising a catheter, a self-sealing input port at a first end of said catheter, magnetic means adjacent the self-sealing input port, and valve means at a second end of said catheter.

Typically, the catheter is a double layer tube comprising an inner conduit compatible with the medication, and an outer conduit made from blood-compatible material.

In a preferred form, the valve means is formed by terminating the inner conduit with at least one outlet therein, and extending the outer conduit beyond the inner conduit. In use, the outer conduit will be collapsed closed under normal internal body pressures. Only when the fluid pressure inside the inner conduit exceeds the internal body pressure will the fluid exit from the outlet(s) through the opening in the outer conduit and into the body.

The self-sealing input port can be filled percutaneously. The input port comprises a volume defined on one side by a gel sealant surrounded by an elastomer through which a syringe may pass, and on the other side by a syringe barrier member through which fluid may pass to the catheter. Preferably, a bacterial filter is located between the syringe barrier and the catheter.

An annular magnet is located around the opening of the input port and covered with a thin sheet of elastomer. The magnet is designed to be located directly under the skin of the user in use. A corresponding annular magnet or ferromagnetic material of reverse polarity is provided on the needle. By bringing the two magnets together, the syringe needle is located in the proper position and held firmly in place while injection of the medication takes place.

In a further broad form there is provided a method of supporting and guiding a syringe needle during insertion and when inserted in a subcutaneous delivery device, said method comprising inserting said subcutaneous delivery device below the skin, said device comprising a catheter, a self-sealing input port at a first end of said catheter, internal magnetic means adjacent the self-sealing input port, and valve means at a second opposite end of said catheter; placing a guide assembly over the skin adjacent said delivery device, said guide assembly including external magnetic means to maintain said guide assembly in approximately fixed relation with said internal magnetic means; inserting said syringe needle through said guide assembly, through the skin and into said input port of said delivery device.

BRIEF DESCRIPTION OF THE DRAWING

Notwithstanding other forms of the invention, a preferred embodiment thereof will now be described with reference to the accompanying drawing which shows a sectional view of the subcutaneous delivery device of the preferred embodiment.

DESCRIPTION OF THE PREFERRED EMBODIMENT

The subcutaneous delivery device comprises a catheter 12 which, in use, remains implanted under the skin 10 of the user. The body of the catheter 12 is constructed from two concentric tubings. The inner tubing 13 is preferably hydrophilic in order to be compatible with the medication, for example insulin. The inner tubing 13 has a very thin wall to provide flexibility. The outer tubing 14 is preferably made from an elastomer such as silicon rubber or polyurethane, which is compatible with blood as has been shown in pacemaker applications. The inner lumen of tubing 13 is terminated blindly. However, holes 15 are provided on the side walls to provide outlet flow of the injected medication. The blind end of the inner tubing is covered by the outer tubing 14 which is stretched over the side holes 15 and collapsed at the interface 16 as a result of the internal body pressure. When the pressure of the medication fluid inside the catheter is greater than the internal body pressure, the medication fluid flows through the side holes 15 to open the interface 16 and exit into the body. Once the medication injection stops, the pressure inside the catheter drops below the internal body pressure and the tubing walls 14 collapse again, closing the interface and preventing any body fluid from flowing into the catheter.

A self-sealing input port is provided at the other end of the catheter 12. The port comprises an elastomer 17 such as silicon rubber surrounding a gel sealant 18. Medication fluid is injected by a syringe 21 which pierces the elastomer 17 and the gel 18. On withdrawal of the syringe 21, the holes will be filled by the high viscosity gel 18. Thus the port may be used many times over. The tip of the syringe 21 is stopped by a metallic perforated strainer 19 which, in addition, prevents any solid debris from entering the catheter 12. The injected medication then passes through a bacterial filter in the form of a porous foam plug 20 in order to prevent any large air bubbles and fibril aggregates entering the catheter. The inner surface of the port is made from material compatible with the medication, e.g. hydrophilic material.

An annular magnet 22 is provided around the opening of the port. The annular magnet 22 is covered with a thin extension of material so that it is isolated from body tissues of fluids. The port assembly is located under the skin. A corresponding annular magnet 23 of reverse polarity is either fixed to the syringe or provides a guide path for the syringe 21. In use, the annular magnet 23 is attached magnetically to the magnet 22 under the skin. A guide hole in a disc attached to the magnet 23 provides a guide path for the syringe needle 21. In this manner, the needle is located correctly and held firmly in place while the medication is injected. Home users of such medication, e.g. diabetics or cancer patients, can inject or infuse themselves confidently as the magnets locate the needle in the proper position. Moreover, the danger of tearing the skin or the elastomers 12, 17 is obviated since the needle is held firmly in position. The invention is particularly suitable for continuous infusion using external pumps.

The foregoing describes only one embodiment of the present invention, and modifications which are obvious to those skilled in the art may be made thereto without departing from the scope of the invention.

I claim:

1. A subcutaneous delivery device comprising a catheter, a self-sealing input port at a first end of said catheter, a magnetic device adjacent the self-sealing input port, the magnetic device comprising a first magnet located subcutaneously and a second magnet adapted to be magnetically held at an exterior location adjacent the first magnet, and valve means at a second opposite end of said catheter.

2. The delivery device of claim 1 wherein said catheter is a double layer tube comprising an inner conduit compatible with the medication and an outer conduit made from blood compatible material.

3. The delivery device of claim 1 wherein said valve means is comprised by the second opposite end of the inner conduit having at least one outlet therein, and an extended outer conduit projecting beyond the inner conduit to sealingly shroud said inner conduit whilst the pressure within said inner conduit is less than internal body pressure.

4. The delivery device of claim 1 where said input port comprises a gel sealant surrounded by an elastomer through which a syringe needle may pass and a syringe barrier member through which fluid may pass to the catheter.

5. The delivery device of claim 4 wherein a bacterial filter is located between the syringe barrier and the catheter.

6. The delivery device of any preceding claim wherein said magnetic means comprises an annular magnet located around the opening of said input port.

7. The delivery device of claim 6 wherein said annular magnet is covered with a thin sheet of elastomer.

8. A subcutaneous delivery assembly comprising a catheter including a self sealing input port at a first end of said catheter, catheter magnetic means adjacent the self sealing input port, valve means at a second opposite end of said catheter; said assembly further including corresponding external needle locator means adapted to be magnetically located adjacent to said catheter magnetic means and separated therefrom by a thin layer of human tissue.

9. The delivery device of claim 8 wherein said needle locator means comprises a stiff disc surrounded by an external annular magnet, said disc having a centrally located hole adapted to guide a syringe needle.

10. The delivery device of claim 9 wherein said catheter magnetic means comprises an internal annular magnet of diameter corresponding to the diameter of said internal annular magnet, said internal annular magnet and said catheter annular magnet being of opposite magnetic polarity.

11. A method of supporting and guiding a syringe needle during insertion of the needle through a layer of skin into a subcutaneous delivery device, said method comprising inserting said subcutaneous delivery device below the skin, said device comprising a catheter, a self-sealing input port at a first end of said catheter, an internal magnetic device adjacent the self-sealing input port, and valve means at a second opposite end of said catheter; placing a guide assembly over the skin adjacent said delivery device, said guide assembly including an external magnetic device to maintain said guide assembly in approximately fixed relation with said internal magnetic device; inserting said syringe needle through said guide assembly, through the skin and into said input port of said delivery device.

* * * * *